(12) United States Patent
Constantz

(10) Patent No.: US 7,658,940 B2
(45) Date of Patent: Feb. 9, 2010

(54) CALCIUM PHOSPHATE CEMENTS COMPRISING AUTOLOGOUS BONE

(75) Inventor: Brent R. Constantz, Cupertino, CA (US)

(73) Assignee: Skeletal Kinetics, LLC, Cupertino, CA (US)

( * ) Notice: Subject to any disclaimer, the term of this patent is extended or adjusted under 35 U.S.C. 154(b) by 115 days.

(21) Appl. No.: 11/694,807

(22) Filed: Mar. 30, 2007

(65) Prior Publication Data

US 2008/0241206 A1    Oct. 2, 2008

(51) Int. Cl.
*A61F 13/00* (2006.01)
*A61K 33/42* (2006.01)
*A01N 59/26* (2006.01)

(52) U.S. Cl. ..................... 424/422; 424/602

(58) Field of Classification Search ............ None
See application file for complete search history.

(56) References Cited

U.S. PATENT DOCUMENTS

| | | | |
|---|---|---|---|
| 5,284,655 A * | 2/1994 | Bogdansky et al. | 424/422 |
| 5,556,399 A | 9/1996 | Huebner | |
| 6,022,354 A * | 2/2000 | Mercuri et al. | 606/80 |
| 6,569,204 B1 * | 5/2003 | Aldecoa | 623/23.51 |
| 6,719,993 B2 | 4/2004 | Constantz | |
| 7,175,858 B2 | 2/2007 | Constantz | |
| 7,252,672 B2 | 8/2007 | Yetkinler et al. | |
| 7,252,833 B2 | 8/2007 | Constantz et al. | |
| 7,252,841 B2 | 8/2007 | Constantz et al. | |
| 7,261,717 B2 | 8/2007 | Yetkinler et al. | |
| 7,261,718 B2 | 8/2007 | Constantz et al. | |
| 2005/0009176 A1 | 1/2005 | Constantz | |
| 2005/0084542 A1 | 4/2005 | Rosenberg et al. | |
| 2006/0282165 A1 | 12/2006 | Pisharodi | |

OTHER PUBLICATIONS

Hausman et al. "Bone Graft System" Surgical Technique, 1996, Acumed, Hillsboro, Oregon.
The Oseoharvester, "Instruction Manual" Osteomed, Addison, Texas.

* cited by examiner

*Primary Examiner*—Ernst V Arnold
(74) *Attorney, Agent, or Firm*—Bret E. Field; Bozicevic, Field & Francis LLP

(57) ABSTRACT

Aspects of the invention include methods for producing flowable compositions, e.g. pastes, that set into calcium phosphate containing products, where the products include autologous bone. Aspects of the invention further include compositions produced by the methods, as well as kits for preparing the same. The subject methods and compositions produced thereby find use in a variety of applications, including hard tissue repair applications.

26 Claims, No Drawings

CALCIUM PHOSPHATE CEMENTS COMPRISING AUTOLOGOUS BONE

INTRODUCTION

Calcium phosphate cements hold great promise for use as structural materials in the orthopedic and dental fields. For example, it is desirable to be able to inject a flowable material into a cancellous bone void and have the material set into a solid calcium phosphate mineral product that is capable of withstanding physiological loads. Materials that set into solid calcium phosphate mineral products are of particular interest as such products can closely resemble the mineral phase of natural bone and are susceptible to remodeling, making such products extremely attractive for use in orthopedics and related fields.

While a large number of different calcium phosphate cement formulations have been developed, there is a continued need for the development of yet more advanced formulations.

SUMMARY

Aspects of the invention include methods for producing flowable compositions, e.g. pastes, that set into calcium phosphate containing products, where the products include autologous bone. Aspects of the invention further include compositions produced by the methods, as well as kits for preparing the same. The subject methods and compositions produced thereby find use in a variety of applications, including hard tissue repair applications.

DETAILED DESCRIPTION

Aspects of the invention include methods and compositions for producing flowable compositions, e.g., pastes, that set into calcium phosphate containing products that include autologous bone. Also provided are the compositions produced by the methods as well as kits for preparing the same. The subject methods and compositions produced thereby find use in a variety of applications, including hard tissue repair applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the is recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the subject invention, the subject methods will be described first, followed by a description of the compositions produced thereby, kits for use in preparing the same and methods for using the subject compositions in methods of hard tissue, e.g. bone repair.

Methods

In the subject methods, dry reactants that include a calcium source and a phosphate source are combined with a setting fluid and autologous bone under conditions sufficient to produce a settable, e.g., flowable, composition that includes autologous bone and sets into a calcium-phosphate containing product, even when immersed in a fluid environment. Each of these different components employed in embodiments of the methods is now reviewed in greater detail.

Dry Reactants

In certain embodiments, the dry reactants include a calcium source and a phosphate source. The dry reactants are typically particulate compositions, e.g., powders, where the particle size of the components of the particulate compositions typically ranges from about 1 to about 1000 microns, usually from about 1 to about 200 microns and more usually from about 1 to about 40 microns.

As mentioned above, the dry reactants include a calcium source and a phosphate source. The calcium source and phosphate source may be present as a single compound or present as two or more compounds. As such, a single calcium phosphate present in the dry reactants may be the calcium source and the phosphate source. Alternatively, two or more compounds may be present in the dry reactants, where the compounds may be compounds that include calcium, phosphate or calcium and phosphate. Calcium phosphate sources of interest that may be present in the dry reactants include: MCPM (monocalcium phosphate monohydrate or $Ca(H_2PO_4)_2.H_2O$); DCPD (dicalcium phosphate dehydrate, brushite or $CaHPO_4.2H_2O$), ACP (amorphous calcium phosphate or $Ca_3(PO_4)_2H_2O$), DCP (or DCPA) (dicalcium phosphate, monetite or $CaHPO_4$), tricalcium phosphate (TCP), including both α- and β- $(Ca_3(PO_4)_2$, tetracalcium phosphate $(Ca_4(PO_4)_2O$, etc. Calcium sources of interest include, but are not limited to: calcium carbonate $(CaCO_3)$, calcium oxide (CaO), calcium hydroxide $(Ca(OH)_2)$ and the like. Phosphate sources of interest include, but are not limited to: Phosphoric acid $(H_3PO_4)$, all soluble phosphates, and the like.

Specific cement compositions of interest include, but are not limited to, those described in U.S. Pat. Nos. 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; 4,429,691; 5,0347,059; 5,336,264; 5,580,623; 6,375,935; 6,719,993 and 7,175,858; and published United States patent application publication Nos.: US-2004-0250730-A1; US-2005-0023171-A1; US-2005-0058717-A1; US-2005-0106260-A1; US-2005-0059979-A1; US-2005-0260278-A1; US-2005-025771 4-A1; US-2006-0292200-A1; US-2006-0100636-A1; the disclosures of which are herein incorporated by reference.

The ratios or relative amounts of each of the disparate calcium and/or phosphate compounds in the dry reactant mixture is one that provides for the desired calcium phosphate product upon combination with the setting fluid and subsequent setting. In many embodiments, the overall ratio (i.e., of all of the disparate calcium and/or phosphate compounds in the dry reactants) of calcium to phosphate in the dry reactants ranges from about 4:1 to 0.5:1, usually from about 2:1 to 1:1 and more usually from about 1.9:1 to 1.33:1.

Setting Fluid

The second component of the subject cement compositions is a setting fluid, as summarized above. The setting fluid can be any of a variety of setting fluids known to those of skill in the art. Setting fluids include a variety of physiologically compatible fluids, including, but not limited to: water (including purified forms thereof), aqueous alkanol solutions, e.g. glycerol, where the alkanol is present in minor amounts, preferably less than about 20 volume percent; pH buffered or non-buffered solutions; solutions of an alkali metal hydroxide, acetate, phosphate or carbonate, particularly sodium, more particularly sodium phosphate or carbonate, e.g., at a concentration in the range of about 0.01 to about 2M, such as from about 0.05 to about 0.5M, and at a pH in the range of about 6 to about 11, such as from about 7 to about 9, including from about 7 to about 7.5; and the like.

Of interest in certain embodiments is a silicate setting fluid, i.e., a setting fluid that is a solution of a soluble silicate. By solution of a soluble silicate is meant an aqueous solution in which a silicate compound is dissolved and/or suspended. The silicate compound may be any compound that is physiologically compatible and is soluble in water. By soluble in water is meant a concentration of at least about 1% usually at least about 2% and more usually at least about 5%, where the concentration of the silicate employed typically ranges from about 0-0.1 to 20%, usually from about 0.01-5 to 15% and more usually from about 5 to 10%.

Silicates of interest include, but are not limited to: sodium silicates, potassium silicates, borosilicates, magnesium silicates, aluminum silicates, zirconium silicates, potassium aluminum silicates, magnesium aluminum silicates, sodium aluminum silicates, sodium methylsilicates, potassium methylsilicates, sodium butylsilicates, sodium propylsilicates, lithium propylsilicates, triethanol ammonium silicates, tetramethanolamine silicates, zinc hexafluorosilicate, ammonium hexafluorosilicate, cobalt hexafluorosilicate, iron hexafluorosilicate, potassium hexafluorosilicate, nickel hexafluorosilicate, barium hexafluorosilicate, hydroxyammonium hexafluorosilicate, sodium hexafluorosilicate and calcium fluorosilicate. The preparation of sodium hexafluorosilicate is described in U.S. Pat. Nos. 4,161,511 and 4,160,012; the disclosures of which are herein incorporated by reference. Of particular interest in many embodiments are solutions of sodium silicate, where the manufacture of dry sodium silicate ($Na_2SiO_3$, $Na_6Si_2O_7$ and $Na_2Si_3O_7$) is described in Faith, Keyes & Clark's INDUSTRIAL CHEMICALS (1975) pp 755-761.

Silicate setting fluids finding use with calcium phosphate cements are further described in U.S. Pat. No. 6,375,935; the disclosure of which is herein incorporated by reference.

In certain embodiments, the solution may further include an amount of phosphate ion, as described in U.S. Application publication no. US-2004-0250730-A1; the disclosure of which is herein incorporated by reference.

Autologous Bone

Another component that is employed in the methods of the invention is autologous bone. By "autologous bone" is meant hard tissue, such as bone, e.g., cancellous, cortical, or combination of both, obtained from the subject which is to receive the cement/autologous bone product. The bone can be harvested from the subject by any convenient means.

In some embodiments, the bone is harvested using a bone harvesting device, such as a commercially available bone harvesting device as sold by Acumed, Osteomed, etc.

In some embodiments, the bone can be harvested using bone harvesting device that includes a bone coring drill, such as the devices described in U.S. Pat. No. 5,556,399 (the disclosure of which is incorporated herein by reference) and sold under the name Bone Frat System by Acumed® (Hillsboro, Oreg.). In using this device, morselized bone is harvested from a convenient location in a subject, e.g., the subject's iliac crest or any other appropriate area. Bone may harvested using any convenient drill size, where four different drill sizes are provided in certain commercial embodiments of the Bone Graft System. The drill size that will provide an adequate amount of bone graft material is selected, and the adaptor provided in the kit is fitted to the power drill. After making an initial incision at the harvest site, the starting punch provided in the kit is used to dimple the bone to serve as a is reference point for the drill tip. The bone is harvested to the desired depth as according to the kit directions, and after harvesting, the drill containing the bone graft material is removed. The bone graft material is extracted using the appropriate wire extractor provided with the kit, and the harvested material is removed from the drill.

In some embodiments, the bone harvesting device employed is the OsteoHarvester™ bone harvesting device sold by Osteomed, Dallas Tex. This device employs a specialized harvester drill to obtain morselized bone fragments, e.g., cortical and/or cancellous, from a subject. In using the OsteoHarvester™ bone harvesting device, hard tissue, e.g., bone, is harvested from any convenient location, e.g., the subject's iliac crest or any other appropriate area. After the harvest site is selected, the suction is turned on, and the drill is actuated. The bone is harvested through as many holes as needed to obtain the necessary amount of morselized bone. After harvesting, a plug is inserted into the reservoir, the drill is detached, and the bone graft material is removed from the reservoir.

Any convenient harvesting device can be employed to obtain an autologous bone composition. The phrase "bone composition" refers to autologous bone that is harvested from a subject, e.g., using an autologous bone harvester, such as the harvesting devices described above. The bone composition employed in the present invention may be in the form of bone particles. "Bone particles" refers to pieces of bone in any variety of sizes, thicknesses and configurations. In some embodiments, the bone particles have a diameter ranging from about 50 μm to about 1000 μm, such as from about 200 μm to 400 μm, including about 200 μm to 300 μm.

The harvested autologous bone may or may not be processed before being combined with a calcium phosphate cement, as described in greater detail below. As such, in certain embodiments, the harvested autologous bone is mixed with the calcium phosphate cement without further processing. In certain embodiments, the autologous bone is processed before use.

Where desired, the autologous bone can be processed by being immersed in a defatting liquid suitable for removing the fatty material from the harvested bone composition. For example, a defatting liquid may be an organic liquid, e.g., acetone and methanol. In some embodiments, the harvested bone graft is immersed in the liquid for about one hour at 20°. Where desired, the bone graft material described above can be dehydrated, to produce a dried autologous bone material. In practicing the subject methods, any convenient method of dehydrating the autologous bone may be used, such as vacuum dehydration, dessication, vacuum dessication, or lyophilization methods.

In certain embodiments, the harvested bone is processed by combining it with a protectant, where the protectant may serve to shield the bone, at least to some extent, from the reactants of the calcium phosphate cement. Of interest in certain embodiments are biocompatible hydrogels, such as the hydrogels disclosed in: U.S. Pat. Nos. 7,022,313; 7,008,633; 6,881,789; 6,800,663; 6,632,457; 6,605,294; 6,552,103; 6,413,539; 6,352,707; 6,333,194; 6,159,496; 6,129,761; 6,107,365; and 5,714,159; the disclosures of which are herein incorporated by reference. The bone can be combined with the protectant in a manner sufficient for the protectant to coat the bone, e.g., by forming an outer layer on the harvested bone.

As such, where desired the bone composition may be combined with a cell protectant gel composition, which gel serves to protect the cells present in the bone particles from damage or death when the particles are combined with the other cement components during preparation. The particles may be coated with or otherwise combined with the gel protectant material using any convenient protocol. An example of a suitable protectant is alginate, e.g., as described in Weir et al., J Biomed Mater Res A. 2006 Jun. 1; 77(3):487-96.

Aspects of the invention also include combining the bone composition with a composition, e.g., a gel composition, that provides, upon setting of the cement composition, a network of passages in the set composition by which oxygen, nutrients, etc., from outside of the composition can easily reach bone particles present inside of the composition. For example, the bone composition may be combined with a hydrogel composition in which the hydrogel composition is in the form of elongated "spaghetti" type structures. When these bone and hydrogel components are combined with the cement composition, the composition will set into a structure in which the hydrogel spaghetti is interspersed throughout the composition as a scaffold or network throughout the composition. When the hydrogel component degrades, passageways or channels remain by which fluid from outside the set composition may reach regions inside the composition, e.g., to facilitate passage of oxygen and nutrients to bone particles inside the composition. Examples of such components include absorbable suture fibers and chitosan, e.g., as described in Zhang et al., J Biomed Mater Res A. 2005 Dec. 15; 75(4):832-40. See also the chitosan or mesh structures disclosed in Xu et al., Biomaterials. 2004 March ; 25(6): 1029-37. Also of interest is a scaffold, such as a chitosan-mannitol-fiber scaffold, e.g., as described in Xu et al., J Biomed Mater Res A. 2004 Mar. 15; 68(4):725-34.

A variety of gel materials may be employed in the above embodiments as protectants and/or network forming structures. Gel materials of interest include, but are not limited to: polylactide and dextran and dextran and maleic acid hydrogels, e.g., as disclosed in published U.S. Patent Application Nos. 20060210602, 20060128918, 20050129734, 20050014252, 20040151752, 20030109647; the chemi-cally modified sodium hyaluronate (HA), carboxymethyl-cellulose (CMC) and polyethylene glycol (PEG) based hydrogel sold under the name of Sepramesh® (Genzyme corporation, Cambridge, Mass.).

In certain embodiments, the methods may further include a backfilling step to fill any void resulting from harvesting of the bone, as described above. While any convenient and compatible bone void filler may be used, in certain embodiments the void resulting from harvesting is filled with an autologous bone/cement composition of the invention, e.g., either flowable or preformed and hardened, as described in greater detail below.

Cement Preparation

In preparing the compositions of the invention from the above components, the dry reactants, setting fluid and autologous bone composition are combined in a ratio sufficient to produce a settable or flowable composition that sets into a calcium phosphate containing product, where the product includes autologous bone. The ratio of the dry reactants to setting fluid (i.e. the liquid to solids ratio) is selected to provide for a "settable" or "flowable" composition, where by "settable" or "flowable" composition is meant a composition that goes from a first non-solid (and also non-gaseous) state to a second, solid state after setting. In certain embodiments, the liquid to solids ratio is chosen to provide for a flowable composition that has a viscosity ranging from that of milk to that of modeling clay. As such, the liquids to solids ratio employed in the subject methods may range from about 0.2 to about 1.0, such as from about 0.3 to about 0.6. Of interest in certain embodiments are methods that produce a paste composition, where the liquid to solids ratio employed in such methods may range form about 0.25 to about 0.5, such as from about 0.3 to about 0.45.

In certain embodiments, the dry reactants, setting fluid and autologous bone composition are combined simultaneously to produce a settable or flowable composition. In other embodiments, the setting fluid and dry reactants are combined to produce a precursor flowable composition, and the precursor flowable composition is then combined with the autologous bone composition.

The amount of autologous bone that is combined with the dry and liquid components, described above, is sufficient to achieve the desired properties of the bone cement/autologous bone composition upon delivery of the composition to an in vivo target site of a subject. Desired properties of the bone cement/autologous bone composition include a composition more similar to native tissue than existing bone cement compositions, with the desired rate of live bone cell incorporation, the desired remodeling rate, and the desired functional and mechanical properties (e.g. setting strength, tensile strength) of a bone cement composition. The amount of autologous bone that is present in the cement may vary, but in certain embodiments ranges from about 5% to about 50% by weight, such as from about 10% to about 40% by weight, including from about 10% to about 20% by weight.

As mentioned above, the requisite amounts of dry reactants, setting fluid and autologous bone (which may be separate from or present in one or both of the dry reactants and setting fluid) are combined under conditions sufficient to produce the flowable product composition. The dry and liquid components may be combined under agitation or mixing conditions, such that a homogenous composition is produced from the dry and liquid components. Mixing may be accomplished using any convenient means, including manual mixing as described in U.S. Pat. No. 6,005,162 and automated mixing as described in WO 98/28068, the disclosures of which are herein incorporated by reference. Also of interest is the device disclosed in U.S. Pat. No. 5,980,482, the disclosure of which is herein incorporated by reference. Also of interest is vibratory mixing, as described in United States Published Patent Application Publication No. US-2005-0058717-A1, the disclosure of which is herein incorporated by reference.

The temperature of the environment in which combination or mixing of the dry and liquid components takes place is sufficient to provide for a product that has desired setting and strength characteristics, and typically ranges from about 0 to 50° C., such as from about 20 to 30° C. Mixing takes place for a period of time sufficient for the flowable composition to be produced, and generally takes place for a period of time ranging from about 15 to 100 seconds, such as from about 15 to about 50 seconds and including from about 15 to about 30 seconds.

The above-described protocols result in a flowable composition that is capable of setting into a calcium phosphate mineral product, as described in greater detail below, where the flowable composition is characterized by including an amount of autologous bone material, where the amount may vary but in representative embodiments ranges from about 5% to about 50% by weight, such as from about 10% to about 40% by weight, including from about 10% to about 20% by weight.

Settable/Flowable Compositions

The flowable compositions produced by the above-described methods are compositions that set into a biologically compatible, and often resorbable and/or remodelable, product, where the product is characterized by including calcium phosphate molecules not present in the initial reactants, i.e., that are the product of a chemical reaction among the initial reactants.

The term flowable is meant to include paste-like compositions, as well as more liquid compositions. Flowable as used herein refers to an injectable or compactable composition. In certain embodiments, the viscosity time of the flowable compositions, defined as time periods under which the mixed composition injects through a standard Luer-lok fitting after mixing, typically ranges up to about 10 minutes, usually up to about 7 minutes, such as up to about 4 minutes. Of interest in certain embodiments are paste compositions that have an injectable viscosity that injects in a time period ranging up to about 5 minutes, such as about up to about 4 minutes. Pastes that stay paste-like for longer periods may be displaced by bleeding bone once implanted into the body, which create a blood interface between the cement and the bone prior to the cement hardening.

The compositions produced by the subject invention set into calcium phosphate mineral containing products. By "calcium phosphate mineral containing" product is meant a solid product that includes one or more, usually primarily one, calcium phosphate mineral. In many embodiments, the calcium phosphate mineral is one that is generally poorly crystalline, so as to be resorbable and, often, remodelable, over time when implanted into a physiologically site. The calcium to phosphate ratio in the product may vary depending on particular reactants and amounts thereof employed to produce it, but typically ranges from about 2:1 to 1.33:1, usually from about 1.8:1 to 1.5:1 and more usually from about 1:7:1 to 1.6:1. Of particular interest in many embodiments are apatitic products, which apatitic products have a calcium to phosphate ratio ranging from about 2.0:1 to 1.33:1, including both hydroxyapatite and calcium deficient analogs thereof, including carbonate substituted hydroxyapatite (i.e. dahilite), etc. The subject paste-like composition is, in certain embodiments, one that is capable of setting into a hydroxyapatitic product, such as a carbonated hydroxyapatite, i.e. dahllite, having a carbonate substitution of from about 2 to about 10%, such as from about 2 to about 8% by weight of the final product.

The period of time required for the compositions to harden or "set" may vary, By set is meant: the Gilmore Needle Test (ASTM C266-89), modified with the cement submerged under 37° C. physiological saline. The set times of the subject cements may range from about 30 seconds to 30 minutes, and in certain embodiments range from about 2 to 15 minutes, such as from about 4 to 12 minutes. In certain embodiments, the flowable composition sets in a clinically relevant period of time. By clinically relevant period of time is meant that the paste-like composition sets in less than about 20 minutes, such as less than about 15 minutes and including less than about 10 minutes, where the composition remains flowable for about 1 minute or more, such as for about 2 minutes or more and, in certain embodiments, for about 5 minutes or more following combination or mixture of the precursor liquid and dry cement components.

The compressive strength of the product into which the flowable composition sets may vary significantly depending on the particular components employed to produce it. Of particular interest in many embodiments is a product that has a compressive strength sufficient for it to serve as at least a cancellous bone structural material. By cancellous bone structural material is meant a material that can be used as a cancellous bone substitute material as it is capable of withstanding the physiological compressive loads experienced by compressive bone under at least normal physiological conditions. As such, the subject flowable paste-like material is one that sets into a product having a compressive strength of about 20 MPa or more, such as about 35 MPa or more, including about 50 MPa or more, as measured by the assay described in Morgan, EF et al., 1997, Mechanical Properties of Carbonated Apatite Bone Mineral Substitute: Strength, Fracture and Fatigue Behavior. J. Materials Science: Materials in Medicine. V. 8, pp 559-570., where the compressive strength of the final apatitic product may be as high as 100 MPa or higher. Inclusion of the silicate in the setting liquid allows lower liquid to solids ratios to be employed which results in significantly higher compressive strengths. Compressive strengths can be obtained that range as high 100 to 200 MPa. In certain embodiments, the resultant product has a tensile strength of about 2 MPa or more, such as about 2.5 MPa or more, including about 4 MPa or more, about 5 MPa or more, e.g., from about 3.5 to about 7 MPa, as determined by the tensile strength assay reported in WO 2006/014886.

In certain embodiments, the resultant product is stable in vivo for extended periods of time, by which is meant that it does not dissolve or degrade (exclusive of the remodeling activity of osteoclasts) under in vivo conditions, e.g., when implanted into a living being, for extended periods of time. In these embodiments, the resultant product may be stable for about 4 months or longer, about 6 months or longer, about 1 year or longer, e.g., 2.5 years, 5 years, etc. In certain embodiments, the resultant product is stable in vitro when placed in an aqueous environment for extended periods of time, by which is meant that it does not dissolve or degrade in an aqueous environment, e.g., when immersed in water, for extended periods of time. In these embodiments, the resultant product may be stable for about 4 months or longer, about 6 months or longer, about 1 year or longer, e.g., 2.5 years, 5 years, etc.

In certain embodiments, the flowable paste-like composition is capable of setting in a fluid environment, such as an in vivo fluid environment at a bone repair site. As such, the flowable paste composition can set in a wet environment, e.g., one that is filled with blood and other physiological fluids. Therefore, the site to which the flowable composition is administered during use need not be maintained in a dry state.

In certain embodiments, the subject cement compositions may be seeded with any of a variety of cells, as described in published U.S. Pat. No. 6,719,993, the disclosure of which is herein incorporated by reference.

In addition, in certain embodiments the compositions include demineralized bone matrix, which may be obtained typically in a lyophilized or gel form and is combined with the cement composition at some prior to implantation. A variety of demineralized bone matrixes are known to those of skill in the art and any convenient/suitable matrix composition may be employed. Alternatively, one or more polymeric agents may be added to the cement, as desired, e.g., collagen, or analogous agents known to be employed in cements.

In certain embodiments, the cements may include one or more collections of contrast particles (for example, for use as tracers during use of the cement), e.g., as described in U.S. Pat. No. 6,273,916; the disclosure of which is herein incorporated by reference.

Molded Objects

In certain embodiments, the autologous bone is first mixed with the calcium phosphate cement and fabricated into shaped material for use in repair of hard tissue defects. Hard tissue defects can include any type of fracture, break, loss of bone or hole in bone, weak or brittle bone, disease or degeneration of bone. The shaped material fabricated from the autologous bone/cement mixture can be used to repair bone, replace bone, improve or strengthen existing bone, or to assist in healing of bone. The shaped material can be used around the site of defect or weakness to support the surrounding tissue, or can be used as a replacement for some or all of a bone structure (e.g. a vertebral body, a long bone such as a tibia or radius, a portion of bone surrounding a joint such as a section of the pelvic bone, or for repair of e.g. the orbit in maxillofacial applications).

The shaped material may be in a variety of shapes and sizes, e.g., for use in implantation into a patient, as desired. Shapes of interest include, but are not limited to: squares, blocks, rectangles, circles, ovals, rods, curved rods, tapered rods, cylinders, planar or curved planar shapes, intervertebral body (e.g., for spinal fusion procedures) and any modification of the above shapes where desired.

In some embodiments, to prepare the molded material ex vivo, the bone/cement mixture is placed into an ex vivo mold, and then allowed to harden or "set" into a formed product. Mold shapes may vary widely, to produce squares, blocks, rectangles, circles, ovals, rods, curved rods, tapered rods, cylinders, planar or curved planar shapes, and any modification of the above shapes where desired, The product may or may not be further processed, e.g., shaped, following setting. As such, in some embodiments, the bone/cement mixture is placed into molds, allowed to harden or "set", and is then fashioned into a formed product in a variety of shapes and sizes for use in implantation into bone. Once formed, the shapes can be further shaped where desired by milling, slicing, cutting, or machining.

An example of such a procedure is preparation of vertebral body spacers using the above methods, which spacers provide both structure and osteoinductive properties. Such spacers are used in any convenient protocol, e.g., according to standard procedures.

In some embodiments, computerized modeling of a specific implant followed by computerized control of the shaping of the implant can be used to provide a shaped bone implant which is custom-fitted to the intended site of application. For example, a mold can replicate a naturally complex bone geometry, such as around a joint, and reproduce a complex three-dimensional shape, such as a scapular bone, a portion of acetabulum that surrounds the hip joint, or for reconstruction of a complex anatomical region such as in maxillofacial applications.

Applications

The subject methods and compositions produced thereby, as described above, find use in applications where it is desired to introduce a flowable material capable of setting up into a solid calcium phosphate product into a physiological site of interest, such as in dental, craniomaxillofacial and orthopedic applications. In orthopedic applications, the cement will generally be prepared, as described above, and introduced to a bone repair site, such as a bone site comprising cancellous and/or cortical bone.

Orthopedic applications in which the cements prepared by the subject system find particular use is in the repair of hard tissue defects, such as the treatment of fractures and/or implant augmentation, in mammalian hosts, particularly humans. In such fracture treatment methodologies, the fracture is first reduced. Following fracture reduction, a flowable composition prepared by the subject system is introduced into the cancellous bone tissue at the site of the defect (e.g. the fracture region). Specific dental, craniomaxillofacial and orthopedic indications in which the subject invention finds use include, but are not limited to, those described in U.S. Pat. No. 6,149,655, the disclosure of which is herein incorporated by reference. In addition to these particular applications described in this U.S. Patent, the subject cement compositions also find use in applications where a sternotomy has been performed. Specifically, the subject cements find use in the closure process of a sternotomy, where the bone fragments are rejoined and wired together, and any remaining cracks are filled with the subject cement. In one embodiment, the subject methods can be used for the treatment of depressed tibia fractures, in which re-elevation of the articular surface and filling of the resulting cancellous defect is desired, with a material which possesses both the mechanical strength needed to support the depressed fragment(s) and appropriate biological properties to match and support native healing.

The above described applications are merely representative of the multitude of applications in which the compositions may find use. The subject methods and compositions can be used in any application where a composition with an increased rate of live bone cell incorporation and a faster remodeling rate is desired.

Kits

Also provided are kits comprising the subject cements, where the dry and liquid components may be present in separate containers in the kit, or some of the components may be combined into one container, such as a kit wherein the dry components are present in a first container and the liquid components are present in a second container, where the containers may or may not be present in a combined configuration, as described in U.S. Pat. No. 6,149,655, the disclosure of which is herein incorporated by reference.

In some embodiments, the kit may include dry reactants comprising a calcium source and a phosphate source, and a setting fluid or components for producing a setting fluid. In some embodiments, the kit may include dry reactants comprising a calcium source and a phosphate source, and a setting fluid or components for producing a setting fluid.

The kit may also contain a bone harvester device. In certain embodiments the kit may contain elements, either disposable or reusable, which may be used for processing the harvested bone such as elements for dehydrating the autologous harvested bone. In some embodiments, the kit may contain mixing elements, either disposable or reusable.

Where desired, the kits may further include a mold, e.g., in the form of an "ice-tray," for producing ex vivo formed objects, such as described above.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXPERIMENTAL

Example 1

A. Materials and Methods

Bovine long bone sections were obtained from a local butcher. The bone material was harvested using the Osteo-Harvester™ device (part#230-002) (Osteomed, Dallas, Tex.) according to the manufacture's instructions. Cancellous segments were identified and a series of holes were drilled with the controller set to the highest speed. Following harvest, the bone pieces were lightly packed into a 3 cc syringe for estimation of the volume harvested. The bone was then added to individual mixes of 5 cc Callos® Impact® calcium phosphate cement (Skeletal Kinetics, Cupertino Calif.) at the end of the one-minute mix by gentle mixing using the provided plastic spatula.

2 cc samples of harvested bone were defatted in 50 mls of acetone/methanol for 1 hour at 20C and evaporated to dryness. The particle size of the dried bone was evaluated by laser diffraction using a Horiba LA-300. Setting strength measurements were made according to Skeletal Kinetics standard procedure (QP110092) (Skeletal Kinetics, Cupertino Calif.) at 4, 6, 10, and 15 minutes, with incubation in pH=7.4 buffer at 32° C. Specimens for evaluating tensile strength were made according to standard procedures and tested following 24 hours incubation in pH=7.4 buffer at 37° C. using the protocol described in WO 2006/014886.

B. Results

Bovine bone harvested using the OsteoHarvester™ bone harvesting device had a mean particle size of 225 μm. Approximately 1 cc bone was collected per 10 drilled holes. The harvested bone was qualitatively described as "fatty". An approximately 10-fold reduction in volume occurred following extraction in acetone/methanol. The setting and tensile strengths are listed in Table 1 below:

TABLE 1

Functional Results: IMPACT ® calcium phospate cement + Bovine Bone

| Sample (IMPACT + cc bovine bone | Set 4 minutes (N) | Set 6 minutes (N) | Set 10 minutes (N) | Set 15 minutes (N) | Tensile (MPa) |
|---|---|---|---|---|---|
| 1 | 572, 466 | 653, 426 | 887, 652 | 826, 721 | 2.1 n = 6, |
| 1.5 | 261, 152 | 374, 202 | 397, 226 | 433, 241 | 1.7 n = 6 high = 2.0 |

Example 2

A. Materials and Methods

Sheep bone was obtained that was fresh frozen (Colorado State Univ. Veterinary Dept.). The femur and tibia were stripped of soft tissue and allowed to thaw at 10° C. overnight. Holes were made using the Accumed™ (Hillsboro, Oreg.) bone harvester device at the diaphyseal/metaphyseal junction. The 8 mm device was used to drill through the proximal cortical bone to the distal wall. Following harvest, the bone pieces were lightly packed in to a 3 cc syringe for estimation of volume harvested. The harvested bone was mixed with Callos® Impact® calcium phosphate cement (Skeletal Kinetics, Cupertino Calif.) at the end of the one-minute mix by gentle mixing using the provided plastic spatula. Setting strength measurements were made according to Skeletal Kinetics standard procedure (QP110092) at 6, 10, 12, and 15 minutes incubation in pH=7.4 buffer at 32° C. Specimens for evaluating tensile strength were made according to standard procedures and tested following 24 hours incubation in pH=7.4 buffer at 37° C. using the protocol described in WO 2006/014886.

Results

Sheep bone harvested using the 8 mm Accumed™ harvesting system had a mean particle size of 225 μm. Approximately 1 cc bone was collected per 3 cm deep hole drilled. An approximately 10-fold reduction in volume occurred following extraction in acetone/methanol. The setting and tensile strengths are listed in Table 2 below:

TABLE 2

Functional Results: IMPACT ® calcium phospate cement + Ovine Bone

| Sample (5cc IMPACT + cc sheep bone | Set 6 minutes (N) | Set 10 minutes (N) | Set 12 minutes (N) | Set 15 minutes (N) | Tensile (MPa) |
|---|---|---|---|---|---|
| 1 | 516, 650 | 980, 692 | 800, 860 | 690, 812 | 3.0 n = 6, |
| 1.5 | 526, 420 | 516, 568 | 618, 418 | 519, 611 | 1.9 n = 6 high |

Example 3

Tibia Defect Model

A total of 16 mature sheep are used for this study. The study protocol is approved by the Institutional Animal Care and Research Committee at Colorado State University. All procedures comply with The Guide for Care and Use of Laboratory Animals, published by the NIH.

Animals are randomized to receive: Callos® cement (experimental group A); Callos® cement plus 1 cc bone (experimental group B); Callos® cement plus 2 cc bone (experimental group C); Callos® cement plus 4 cc bone (experimental group D). Animals are anesthetized using intravenous Pentothal at 25 mg/kg, followed by intubation and general anesthesia using halothane, 2%. Both hind limbs are prepared for surgery and sterilely draped under aseptic conditions.

The proximal femur and tibia are exposed using a medial parapatellar approach. The tibial eminence is exposed and an 8 mm core drill is used to remove a cylindrical segment of bone approximately 2.5 cm deep by drilling in a lateral to medial direction while not penetrating the medial cortex. Additional corticocancellous reamings are taken using the same core drill. Following harvest, bone tissue is lightly packed into a 3 cc syringe for estimation of volume harvested. Bone is then added to individual mixes of 5 cc Callos® Impact® kits at the end of the prescribed one-minute mix by gentle mixing using the provided plastic spatula. The autologous bone/cement mixture is used to fill the tibial defect by either hand packing or with a straight barrel delivery syringe supplied with the cement. The skin and surgical access site is closed in routine fashion and sterile bandages applied to the limbs. Postoperative analgesics are given for 1 week and animals are allowed to freely ambulate.

The distal femur is exposed using a medial parapatellar approach. The distal femoral condyle is exposed and a core drill is used to remove a cylindrical segment of bone approximately 2.5 cm deep by drilling in a lateral to medial direction while not penetrating the medial cortex. Additional corticocancellous reamings are taken using the same core drill. Following harvest, bone tissue is lightly packed into a 3 cc syringe for estimation of volume harvested. Bone is then added to individual mixes of 5 cc Callos® Impact® cement kits at the end of the prescribed one-minute mix by gentle mixing using the provided plastic spatula. The autologous bone/cement mixture is used to fill the femoral defect by either hand packing or with a straight barrel delivery syringe supplied with the cement. The skin and surgical access site is closed in routine fashion and sterile bandages applied to the limbs. Post-operative analgesics are given for 1 week and animals are allowed to freely ambulate Results A. Histology:

Following mechanical testing, the tibial plateau and proximal femur are fixed in 70% ethanol. Fixed specimens are dehydrated in graded ethanol to 100% and infiltrated with methylmethacrylate. Thin sections are taken at 10-15 microns using the Exakt system, stained with von geison/trichrome and imaged under standard light microscopy. Morphometric measurements taken include: percent (%) bone within the defect; remodeled area (%); new bone formation and cellular necrosis.

Following implantation intervals of 1 month, 3 months, 6 months, and 12 months, necropsies are performed following barbiturate overdose and specimens taken immediately for histological processing. Tibia and femur defects filled with the Callos/autologous bone mixture are harvested, processed, and evaluated for cellular remodeling and cell viability by standard bone histology techniques.

B. In Vitro and In Vivo Cell Viability

Following mixing of bone with Callos® calcium phosphate cement, approximately 1 cc of cement/bone mixture is placed in a 15 cc sterile centrifuge tube and 37° C. alpha minimum essential cell culture media (alpha-MEM) containing 10% sheep serum added to fill the tube. Cultures are maintained under 5% $CO_2$ at 37° C. and assayed at time points of post mix, 1 hour, 3 hours, 12 hours, and 24 hours incubation. Samples are stained using Calcein AM/Ethidium homodimer-1 that is a live/dead fluorescent stain (Molecular Probes, L3224). Following staining, samples are examined under confocal laser microscopy. Live cells appear green under 494 nm excitation/517 nm emission, while dead cells appear red using 528 nm excitation/617 nm emission.

The above compositions exhibit improved features relative to cement compositions that do not include autologous bone. For example, the compositions exhibit osteoinductive properties. For ex vivo formed structures, the structures provide both structural properties (e.g., spacer properties, such as intervertebral body spacers for use in spinal fusions) and osteoinductive properties. For example, when used with an appropriate mold, intaroperative spacers for implantation in the disc space during procedures such as Posterior Lateral Interbody Fusion & Transverse Lateral procedures are readily obtained. In certain embodiments, these spacers are osteoinductive implants which can be delivered to completely cover the vertebral endplates and maintain disc space height during procedures such as Posterior Lateral & Transverse Lateral Fusion procedures. In certain embodiments, an osteoinductive flowable implant that completely fills the disc space and maintains annular tension is provided.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of producing a flowable composition that sets into a hardened calcium phosphate containing product suitable for implantation into a subject, said method comprising:
    combining:
    (a) a setting fluid wherein said setting fluid is a solution of a soluble silicate;
    (b) dry reactants comprising a calcium source and a phosphate source; and
    (c) from about 5% to about 50% by weight of a bone composition autologous to said subject, wherein said bone composition comprises a plurality of bone particles wherein said bone particles have a diameter ranging from about 20 to about 1000 μm;
    in a ratio of (a) to (b) sufficient to produce said flowable composition that sets into a calcium phosphate containing product.

2. The method according to claim 1, wherein said setting fluid, dry reactants and bone composition are combined simultaneously.

3. The method according to claim 1, wherein said setting fluid and dry reactants are combined to produce a precursor flowable composition and said precursor flowable composition is then combined with said bone composition.

4. The method according to claim 1, wherein said method further comprises obtaining said bone composition from said subject.

5. The method according to claim 4, wherein said obtaining comprises harvesting bone from said subject using a bone harvesting device.

6. The method according to claim 5, wherein said bone harvesting device comprises a bone coring drill.

7. The method according to claim 5, wherein said bone harvesting device comprises a harvester drill designed to obtain morselized bone fragments from a subject.

8. The method according to claim 4, wherein said bone composition is combined with a cell protectant prior to combination with said setting fluid and dry reactants.

9. The method according to claim 4, wherein said bone composition is combined with a gel prior to combination with said setting fluid and dry reactants.

10. The method according to claim 9, wherein said gel is a biodegradable gel that produces a network structure in said flowable composition.

11. The method according to claim 10, wherein said gel network structure allows oxygen and nutrients to reach bone particles present inside of said composition.

12. The method according to claim 1, wherein said flowable composition is a paste.

13. The method according to claim 1, wherein said flowable composition sets into said calcium phosphate containing product in a period of time ranging from 30 seconds to 30 minutes.

14. The method according to claim 1, wherein said calcium phosphate containing product has a compressive strength ranging from 10 to 100 MPa.

15. The method according to claim 14, wherein said in vivo target site is a reduced fracture site.

16. The method according to claim 1, wherein said method further comprises placing said composition in an ex vivo mold and allowing said composition to set in said mold into a formed product.

17. The method according to claim 16, wherein said composition further comprises implanting said formed product into said subject.

18. The method according to claim 16, wherein said formed product is an intervertebral body spacer 19. The method according to claim 1, wherein said method further comprises delivering said flowable composition to an in vivo target site of said subject.

20. A flowable composition that sets into a hardened calcium phosphate containing product and comprises autologous bone particles produced by the method of claim 1.

21. The composition according to claim 20, wherein said calcium phosphate containing product has a compressive strength ranging from 10 to 100 MPa.

22. A method of repairing a hard tissue defect, said method comprising:
    (a) preparing a flowable composition according to claim 20; and
    (b) applying said flowable composition to the site of said defect; to repair said hard tissue defect.

23. A kit for use in a preparing a flowable composition that sets in an in vivo fluid environment in a subject into a calcium phosphate product containing bone autologous to said subject, said kit comprising:
    (a) dry reactants comprising a calcium source and a phosphate source;
    (b) a setting fluid or components for producing the same; and
    (c) instructions for combining said components with autologous bone in a manner according to the method of claim 1.

24. The kit according to claim 23, wherein said kit further comprises an autologous bone harvester.

25. The kit according to claim 23, wherein said kit further comprises a mold.

26. The kit according to claim 25, wherein said mold is a mold for an intervertebral body spacer.

* * * * *